United States Patent
DeLuca et al.

(10) Patent No.: US 7,704,980 B2
(45) Date of Patent: Apr. 27, 2010

(54) TREATMENT OF INFLAMMATORY BOWEL DISEASE WITH 2-METHYLENE-19-NOR-VITAMIN D COMPOUNDS

(75) Inventors: Hector F. DeLuca, Deerfield, WI (US); Margherita Cantorna, State College, PA (US)

(73) Assignees: Wisconsin Alumni Research Foundation, Madison, WI (US); The Penn State Research Foundation, University Park, PA (US)

( * ) Notice: Subject to any disclaimer, the term of this patent is extended or adjusted under 35 U.S.C. 154(b) by 1129 days.

(21) Appl. No.: 10/680,881

(22) Filed: Oct. 8, 2003

(65) Prior Publication Data

US 2005/0080059 A1 Apr. 14, 2005

(51) Int. Cl.
*A61K 31/59* (2006.01)
*C07C 401/00* (2006.01)

(52) U.S. Cl. .................................. 514/167; 614/167
(58) Field of Classification Search ................. 514/167
See application file for complete search history.

(56) References Cited

U.S. PATENT DOCUMENTS

| 5,583,125 | A | | 12/1996 | Steinmeyer et al. |
| 5,663,157 | A | | 9/1997 | Steinmeyer et al. |
| 5,843,928 | A | * | 12/1998 | Deluca et al. ............... 514/167 |
| 5,981,597 | A | * | 11/1999 | Wu ............................. 514/616 |
| 6,358,939 | B1 | * | 3/2002 | Hayes et al. ................ 514/167 |
| 6,392,071 | B1 | * | 5/2002 | DeLuca et al. .............. 552/653 |

FOREIGN PATENT DOCUMENTS

WO WO01/92221 A1 * 12/2001

OTHER PUBLICATIONS

Keiji, Patent Abstracts of Japan, Accession No. XP002167821, Treating Agent Containing Activated Vitamin D, vol. 018, No. 093, Feb. 16, 1994, Abstract only.

* cited by examiner

*Primary Examiner*—Sreeni Padmanabhan
*Assistant Examiner*—Layla Soroush
(74) *Attorney, Agent, or Firm*—Andrus, Sceales, Starke & Sawall, LLP

(57) ABSTRACT

A method of preventing and/or treating inflammatory bowel disease, particularly ulcerative colitis and Crohn's disease, is disclosed. The method involves administering a 2-methylene-19-nor-vitamin D compound in an amount effective to treat the disease. The administration of a 2-methylene-19-nor-vitamin D compound also prevents the development of or delays the onset of inflammatory bowel disease in susceptible individuals. The preferred compounds are 1α-hydroxy-2-methylene-19-nor-homopregnacalciferol and 2-methylene-19-nor-20(S)-1α,25-dihydroxyvitamin $D_3$.

5 Claims, No Drawings

TREATMENT OF INFLAMMATORY BOWEL DISEASE WITH 2-METHYLENE-19-NOR-VITAMIN D COMPOUNDS

BACKGROUND OF THE INVENTION

This invention relates to vitamin D compounds, and more particularly to the use of 2-methylene-19-nor-vitamin D compounds to prevent and/or treat inflammatory bowel disease.

The natural hormone, $1\alpha,25$-dihydroxyvitamin $D_3$ and its analog $1\alpha,25$-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Inflammatory bowel diseases (IBD) are immune mediated diseases of unknown etiology affecting the gastrointestinal (GI) tract. There are at least two distinct forms of IBD, ulcerative colitis and Crohn's disease. IBD are chronic recurring illnesses most commonly involving inflammation of the terminal ileum and colon, although these diseases can also affect many sites throughout the alimentary tract. Clearly, genetic factors predispose individuals to development of IBD (Podolosky 1991). In addition, the environment contributes to IBD development, and there is reason to believe that vitamin D may be an environmental factor which affects IBD. Vitamin D from sunlight exposure is less in areas where IBD occurs most often, as IBD is most prevalent in northern climates such as North America and Northern Europe (Podolosky 1991, Sonnenberg et al. 1991). A major source of vitamin D results from its manufacture via a photolysis reaction in the skin, and vitamin D available from sunlight exposure is significantly less in northern climates, and especially low during the winter (Clemens et al. 1982, DeLuca 1993). Dietary intake of vitamin D is problematic since there are few foods which are naturally rich in vitamin D. Weight loss occurs in 65-75% of patients diagnosed with Crohn's disease and 18-62% of patients with ulcerative colitis (Fleming 1995, Geerling et al. 1998). Vitamin deficiencies in general and vitamin D deficiency in particular have been shown to occur in IBD patients (Andreassen et al. 1998, Kuroki et al. 1993). To date the possible association between vitamin D status and the incidence and severity of IBD in humans or animals has not been studied. The anecdotal information suggests that vitamin D status could be an environmental factor affecting the prevalence rate for IBD and that the correlation warrants investigation.

The identification of vitamin D receptors in peripheral blood mononuclear cells sparked the early interest in vitamin D as an immune system regulator (Bhalla et al. 1983, Provvedini et al. 1983). In particular the CD4+ Th cells have vitamin D receptors and are therefore targets for vitamin D (Veldman et al. 2000). Hormonally active vitamin D (1,25-dihydroxycholecalciferol) suppressed the development of at least two experimental autoimmune diseases (Cantorna et al. 1996, Cantorna et al. 1998). In vitro 1,25-dihydroxycholecalciferol inhibited T cell proliferation and decreased the production of interleukin (IL)-2, interferon (IFN)-γ, and tumor necrosis factor (TNF)-α (Lemire-1992). In vivo 1,25-dihydroxycholecalciferol injections were shown to inhibit the delayed type hypersensitivity reaction associated with the type-1 helper T (Th1) cell response (Lemire et al. 1991, Lemire et al. 1992). Vitamin D is a potent regulator of the immune system in general and T cells specifically.

For IBD, the immune mediated attack is against the GI tract (Niessner and Volk 1995, Podolosky 1991). T cells, which preferentially produce the Th1 cytokines (IL-2, IFN-γ, and TNF-α), have been shown to transfer Crohn's-like symptoms to naive mice (Aranda et al. 1997, Bregenholt and Claesson 1998) and the production of Th1 cytokines is associated with IBD in humans as well (Niessner and Volk 1995). 1,25-dihydroxycholecalciferol treatment has been shown to suppress the development of other T cell mediated experimental autoimmune diseases (multiple sclerosis, and arthritis; Cantorna et al. 1996, Cantoma et al. 1998). The hypothesis that vitamin D (through the production of 1,25-dihydroxycholecalciferol) would suppress the development and progression of IBD thus seemed credible. Cantorna in PCT application WO 01/42205 and Hayes et al in U.S. Pat. No. 6,358,939 both have reported that $1,25(OH)_2D_3$ can prevent IBD in IL-10 knock-out mice. However, hypercalcemia can be a significant problem when $1,25(OH)_2D_3$ is used to treat IBD.

Standard treatments of patients with IBD include short-term high dose and long term low dose prednisone use (Podolosky 1991, Andreassen et al. 1998). Prednisone and other corticosteroid therapies result in a decreased bone mineral density and many times result in higher risks for vertebral fracture (Andreassen et al. 1997, Andreassen et al. 1998). Vitamin D supplementation of patients on corticosteroids has been shown to prevent steroid induced bone loss (Buckley et al. 1996). The hormonally active form of vitamin D (1,25-dihydroxycholecalciferol) is known to increase bone mineralization when given to experimental animals (Cantorna et al. 1998) and people (Ongphiphadhanakul et al. 2000). Thus a further benefit of vitamin D and or 1,25-dihydroxycholecalciferol supplementation may be the maintenance of bone mineral density.

SUMMARY OF THE INVENTION

The present invention provides new vitamin D analogs that can prevent and/or treat IBD. The present invention is thus directed toward a method of preventing inflammatory bowel diseases (IBD) in susceptible individuals and treating patients with IBD by administering an amount of a 2-methylene-19-nor-vitamin D compound, preferably either $1\alpha$-hydroxy-2-methylene-19-nor-homopregnacalciferol (hereinafter referred to as "2-MP") or 2-methylene-19-nor-20(S)-$1\alpha,25$-dihydroxyvitamin $D_3$ (hereinafter referred to as "2-MD"), or a combination of both, effective to prevent IBD development or to diminish IBD symptoms, respectively. 2-MP is substantially non-calcemic and 2-MD can be used at such a low dose that hypercalcemia does not result thus avoiding the primary disadvantage of $1,25(OH)_2D_3$. The method comprises selecting an IBD patient and administering a sufficient amount of the vitamin D analog to the patient such that the IBD symptoms are abated.

Structurally the 2-methylene-19-nor-vitamin D compounds found useful to prevent and/or treat IBD are characterized by the general formula I shown below:

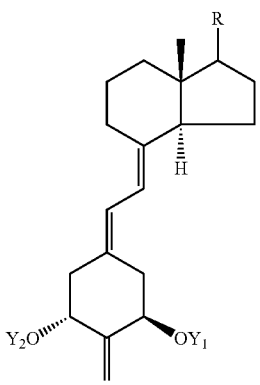

I where $Y_1$ and $Y_2$, which may be the same or different, are each selected from the group consisting of hydrogen and a hydroxy-protecting group, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

4 where the stereochemical center (corresponding to C-20 in steroid numbering) may have the R or S configuration, (i.e. either the natural configuration about carbon 20 or the 20-epi configuration), and where Z is selected from Y, —OY, —CH$_2$OY, —C≡CY and —CH=CHY, where the double bond may have the cis or trans geometry, and where Y is selected from hydrogen, methyl, —COR$^5$ and a radical of the structure:

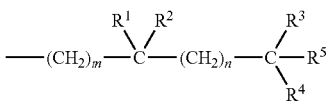

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$ taken together may represent an oxo group, or an alkylidene group =CR$^2$R$^3$, or the group —(CH$_2$)$_p$—, where p is an integer from 2 to 5, and where $R^3$ and $R^4$ taken together represent an oxo group, or the group —(CH$_2$)$_q$— where q is an integer from 2 to 5, and where $R^5$ represents hydrogen, hydroxy, protected hydroxy, or $C_{1-5}$ alkyl and wherein any CH-group at positions 20, 22, or 23 in the side chain may be replaced by a nitrogen atom, or where any of the groups —CH(CH$_3$)—, —(CH$_2$)$_m$—, —C(R$^1$R$^2$)— or (CH$_2$)$_n$— at positions 20, 22, and 23, respectively, may be replaced by an oxygen or sulfur atom.

The wavy line to the methyl substituent at C-20 indicates that carbon 20 may have either the R or S configuration.

Specific important examples of side chains with natural 20R-configuration are the structures represented by formulas (a), b), (c), (d), (e), (f), (g) and (h) below, i.e. the side chain as it occurs in 25-hydroxyvitamin D$_3$ (a); vitamin D$_3$ (b); 25-hydroxyvitamin D$_2$ (c); vitamin D$_2$ (d); the C-24 epimer of 25-hydroxyvitamin D$_2$ (e); pregnacalciferol (f); homopregnacalciferol (g); and bis-homopregnacalciferol (h).

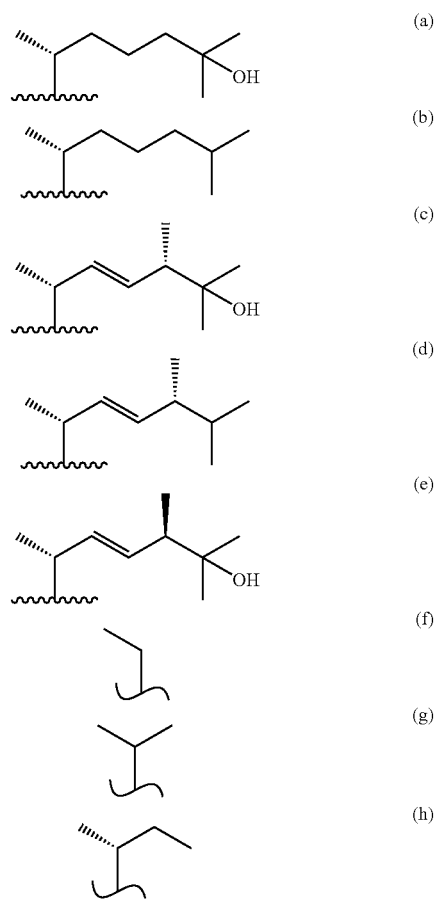

Vitamin D analogs such as but not limited to the following are particularly preferred: 1α-hydroxy-2-methylene-19-nor-homopregnacalciferol (see formula II and referred to herein as "2-MP") and 2-methylene-19-nor-20(S)-1α,25-dihydroxyvitamin D$_3$ (see formula III and referred to herein as "2-MD"). In a most preferred form of the invention, the compound is 2-MP.

The above compounds may be present in a composition to prevent and/or treat IBD in an amount from about 0.01 μg/gm to about 100 μg/gm of the composition, and may be administered topically, transdermally, orally or parenterally in dosages of from about 0.01 µg/day to about 10 mg/day per 160 pound person.

A preferred dose of vitamin D compound for the present invention is that which is effective to prevent and/or treat IBD and further is the maximum that a patient can tolerate and not develop serious hypercalcemia. The preferred dose is between 0.1 µg and 10 mg per day per 160 pound patient depending on the calcemic properties of the vitamin D analog used. If the patient has calcium intakes of above 800 mg/day, and the vitamin D analog is calcemic (like 1α,25-dihydroxyvitamin $D_3$) doses over 2 µg per day per 160 pound patient are not preferred. If the patient is on a low calcium diet and/or takes the dose late at night, higher doses would be possible and may be preferred, especially if the compound is non-calcemic. In this embodiment of the invention, the amount of compound administered could be as high as 10 mg per day per 160 pound patient. A preferred dose would be 0.5 µg to 10 mg per day per 160 pound patient for a non-calcemic compound and 0.1 µg/day to 50.0 g/day for a compound that has a tendency to raise serum calcium.

DETAILED DESCRIPTION OF THE INVENTION

As used in the description and in the claims, the term "hydroxy-protecting Group' signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. The term "alkylidene" refers to any of a series of unsaturated open-chain hydrocarbons of 1 to 10 carbons containing a double bond and corresponding in composition to the general formula $C_nH_{2n}$.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

The terms "vitamin D compound", "vitamin D analog" and/or "2-methylene-19-nor-vitamin D compounds" refers to the compounds defined by general formula I. It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are both ethyl groups. Likewise, the term "26,27-diethyl" refers to the addition of an ethyl group at the 26 and 27 positions so that $R^3$ and $R^4$ are both propyl groups.

In the following lists of compounds, a methylene substituent is attached at the carbon 2 position of the A-ring and thus the term "2-methylene" is used in the nomenclature. Likewise, in formula I there are two hydrogen atoms bonded to carbon 10 of the A-ring and therefore the term "19-nor" proceeds each of the named compounds. In addition, if the methyl group attached at the carbon 20 position is in its epi or unnatural configuration, the term "20(S)" or "20-epi" should be included in each of the following named compounds. The named compounds could also be of the vitamin $D_2$ and/or $D_4$ type if desired.

Specific and preferred examples of the vitamin D compounds of structure I when the side chain is unsaturated are:
2-methylene-19-nor-1α-hydroxy-22-dehydrovitamin $D_3$;
2-methylene-19-nor-1,25-dihydroxy-22-dehydrovitamin $D_3$;
2-methylene-19-nor-1,24-dihydroxy-22-dehydrovitamin $D_3$;
2-methylene-19-nor-24-homo-1,25-dihydroxy-22-dehydrovitamin $D_3$;
2-methylene-19-nor-24-dihomo-1,25-dihydroxy-22-dehydrovitamin $D_3$;
2-methylene-19-nor-24-trihomo-1,25-dihydroxy-22-dehydrovitamin $D_3$;
2-methylene-19-nor-26,27-dimethyl-24-homo-1,25-dihydroxy-22-dehydrovitamin $D_3$;
2-methylene-19-nor-26,27-dimethyl-24-dihomo-1,25-dihydroxy-22-dehydrovitamin $D_3$;
2-methylene-19-nor-26,27-dimethyl-24-trihomo-1,25-dihydroxy-22-dehydrovitamin $D_3$;
2-methylene-19-nor-26,27-diethyl-24-homo-1,25-dihydroxy-22-dehydrovitamin $D_3$;
2-methylene-19-nor-26,27-diethyl-24-dihomo-1,25-dihydroxy-22-dehydrovitamin $D_3$;
2-methylene-19-nor-26,27-diethyl-24-trihomo-1,25-dihydroxy-22-dehydrovitamin $D_3$;
2-methylene-19-nor-26,27-dipropyl-24-homo-1,25-dihydroxy-22-dehydrovitamin $D_3$;
2-methylene-19-nor-26,27-dipropyl-24-dihomo-1,25-dihydroxy-22-dehydrovitamin $D_3$; and
2-methylene-19-nor-26,27-dipropyl-24-trihomo-1,25-dihydroxy-22-dehydrovitamin $D_3$.

Specific and preferred examples of the vitamin D compounds of structure I when the side chain is saturated are:
2-methylene-19-nor-1α-hydroxyvitamin $D_3$;
2-methylene-19-nor-1,25-dihydroxyvitamin $D_3$;
2-methylene-19-nor-1,24-dihydroxyvitamin $D_3$;
2-methylene-19-nor-24-homo-1,25-dihydroxyvitamin $D_3$;
2-methylene-19-nor-24-dihomo-1,25-dihydroxyvitamin $D_3$;
2-methylene-19-nor-24-trihomo-1,25-dihydroxyvitamin $D_3$;
2-methylene-19-nor-26,27-dimethyl-24-homo-1,25-dihydroxyvitamin $D_3$;
2-methylene-19-nor-26,27-dimethyl-24-dihomo-1,25-dihydroxyvitamin $D_3$;
2-methylene-19-nor-26,27-dimethyl-24-trihomo-1,25-dihydroxyvitamin $D_3$;
2-methylene-19-nor-26,27-diethyl-24-homo-1,25-dihydroxyvitamin $D_3$;
2-methylene-19-nor-26,27-diethyl-24-dihomo-1,25-dihydroxyvitamin $D_3$;

2-methylene-19-nor-26,27-diethyl-24-trihomo-1,25-dihydroxyvitamin $D_3$;
2-methylene-19-nor-26,27-dipropyl-24-homo-1,25-dihydroxyvitamin $D_3$;
2-methylene-19-nor-26,27-dipropyl-24-dihomo-1,25-dihydroxyvitamin $D_3$; and
2-methylene-19-nor-26,27-dipropyl-24-trihomo-1,25-dihydroxyvitamin $D_3$.

Specific and preferred examples of the vitamin D compounds of structure I when the side chain is truncated are:
2-methylene-19-nor-1α-hydroxy-pregnacalciferol;
2-methylene-19-nor-1α-hydroxy-homopregnacalciferol; and
2-methylene-19-nor-1α-hydroxy-bishomopregnacalciferol.

As noted previously, the preferred compound is either 1α-hydroxy-2-methylene-19-nor-homopregnacalciferol (2-MP) having the following formula II:

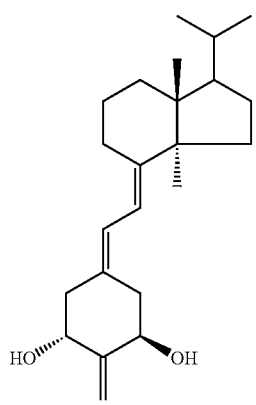

II or is 2-methylene-19-nor-20(S)-1α,25-dihydroxyvitamin $D_3$ (2-MD) having the following formula III:

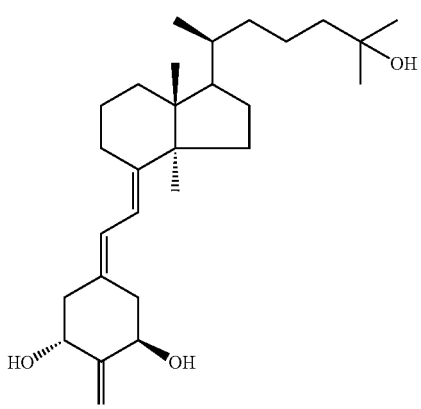

III

The most preferred compound is 2-MP.

The preparation of vitamin D compounds having the basic structure I can be accomplished by a common general method, i.e. the condensation of a bicyclic Windaus-Grundmann type ketone IV with the allylic phosphine oxide V to the corresponding protected protected vitamin D analogs VI followed by deprotection, if desired, at C-1 and C-3 in the latter compounds to obtain the 2-methylene-19-nor-vitamin D compounds of structure I:

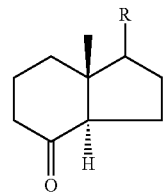

IV

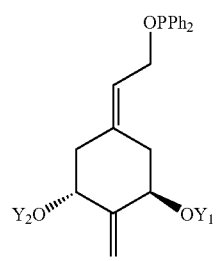

V

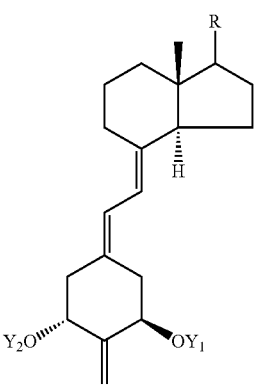

VI

In the structures IV, V, and VI groups $Y_1$, $Y_2$ and R represent groups defined above; Y I and Y2 are preferably hydroxy-protecting groups, it being also understood that any functionalities in R that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure IV are known, or can be prepared by known methods. Specific important examples of such known bicyclic ketones are the structures with the side chains (a), (b), (c) and (d) described above, i.e. 25-hydroxy Grundmann's ketone (i) [Baggiolini et al., J. Org. Chem, 51, 3098 (1986)]; Grundmann's ketone (j) [Inhoffen et al., Chem. Ber. 90, 664 (1957)]; 25-hydroxy Windaus ketone (k) [Baggiolini et al., J. Org. Chem., 51, 3098 (1986)] and Windaus ketone (l) [Windaus et al., Ann., 524, 297 (1936)]:

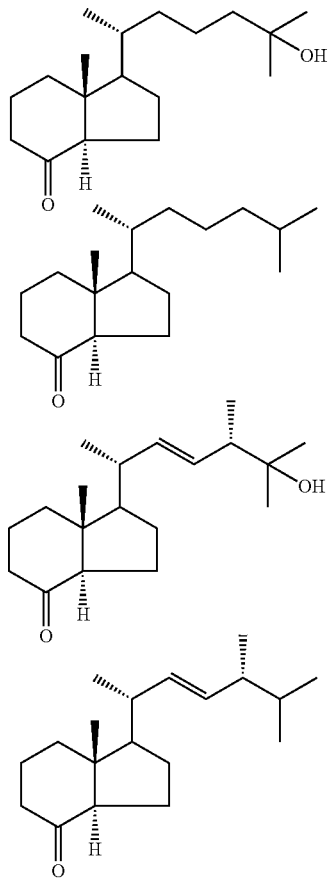

For the preparation of the required phosphine oxides of general structure V, a synthetic route has been developed starting from a methyl quinicate derivative, easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I is illustrated and described more completely in U.S. Pat. No. 5,945,410 issued Aug. 31, 1999 and entitled "2-Alkyl-19-Nor-Vitamin D Compounds" the specification of which is specifically incorporated herein by reference.

This invention is further described by the following illustrative example. This example demonstrates that vitamin D deficiency exacerbates symptoms of IBD in IL-10 KO mice. Vitamin D deficiency also exacerbated the symptoms of enterocolitis in the animal model. These data predict that both forms of IBD (ulcerative colitis and Crohn's disease) are amenable to prevention and treatment with 2-methylene-19-nor-vitamin D compounds of structure I, and particular efficacy is shown by 2-MP and 2-MD.

EXAMPLE 1

Recently a number of transgenic animals have been developed in which IBD symptoms occur spontaneously. One of the best animal models for Crohn's disease is the IL-10 knockout (KO) mouse (Kuhn et al. 1993, Mac Donald 1994). In conventional animal facilities, the IL-10 KO micedevelop enterocolitis within 5-8 weeks of life (Kuhn et al. 1993). Approximately 30% of the IL-10 KO mice die following the development of severe anemia and weight loss (Kuhn et al. 1993). The enterocolitis which develops in IL-10 KO mice is due to an uncontrolled immune response to conventional microflora since germfree IL-10 KO mice do not develop disease. In addition mice raised in specific pathogen free facilities develop milder disease which doesn't result in the death of the mice (Kuhn et al. 1993). There are limitations involved in studying IL-10 KO mice as a model of IBD. If vitamin D is a regulator of IL-10 production then the results in this animal model may not represent what may happen in a "normal" immune response. However patients with Crohn's disease show similar symptoms, have depressed IL-10 production, and have been successfully treated with IL-10 (Narula et al. 1998).

Summary of Experiment

Vitamin D deficient IL-10 KO mice were randomly distributed into one of 4 groups. Controls remained vitamin D deficient for the entire 9-10 weeks of the experiment. Mice treated with 1α,25-dihydroxyvitamin $D_3$ (hereinafter "1,25 $(OH)_2D_3$") were vitamin D deficient for 5 weeks and then received 5 ng/d in the diet for the remainder of the experiment. 2-MP treated mice were vitamin D deficient for 5 weeks and then received 720 ng/d in the diet for the remainder of the experiment. 2-MD treated mice were vitamin D deficient for 5 weeks and then received 0.12 ng/d in the diet for the remainder of the experiment. VDR KO IL10KO mice were bred with VDR KO mice and the double IL10/VDR KO mice are compared here.

| Treatment | Incidence[1](# with colitis/n) | Serum Calcium (mg %) | SI/BW[2] (%) | BW (g) |
|---|---|---|---|---|
| VDR KO[3] | 11/11[a] | 9.3 ± 0.5[a,c] | 7.7 ± 0.5[a] | 8.1 ± 3.0[a] |
| Control | 27/33[b] | 6.9 ± 0.4[b] | 8.0 ± 0.8[a] | 12.4 ± 2.3[b] |
| 1,25(OH)$_2$D$_3$ | 1/28[c] | 8.9 ± 0.3[a] | 5.8 ± 0.3[b] | 20.8 ± 0.5[c] |
| 2-MP | 0/8[c] | 9.3 ± 0.5[a,c] | 5.4 ± 0.3[b] | 20.2 ± 0.5[c] |
| 2-MD | 0/9[c] | 10.2 ± 0.5[c] | 5.3 ± 0.1[b] | 20.8 ± 1.0[c] |

[1]Incidence defined as SI/BW % of greater than 6.5. Small intestine weight = SI, body weight = BW. All mice are of the C57BL/6 strain and the SI/BW % values from these wildtype mice are 5-6.
[2]This value represents the % SI/BW of all mice in the group.
[3]IL-10/VDR double KO mice begin to show symptoms of colitis at 3-5 weeks of age. They bleed rectally and by 5 weeks of age all of the mice are dead.

Values with different subscripts are significantly different (P<0.05) from each other.

CONCLUSIONS

Vitamin D deficiency results in accelerated and severe colitis in IL-10 KO mice. The active form of vitamin D and vitamin D analogs such as 2-MP and 2-MD inhibit the development of colitis in these IL-10 KO mice. The serum calcium values and the body weights of the mice on the vitamin D analogs are within the normal range for mice. The 2-MD analog was associated with a slight increase in serum calcium at this dose. The vitamin D analogs 2-MD and 2-MP are effective at inhibiting and/or preventing the development of colitis symptoms in this experimental model of IBD. 2-MP is preferred over 2-MD because it did not significantly change serum calcium yet clearly blocked the development of the disease.

Standard treatments of patients with IBD include short-term high dose and long term low dose prednisone use (Andreassen et al. 1998, Podolosky 1991). Prednisone and other corticosteroid therapies result in a decreased bone mineral density and many times result in higher risks for vertebral fracture (Andreassen et al. 1997, Andreassen et al. 1998). Vitamin D supplementation of patients on corticosteroids has been shown to prevent steroid induced bone loss (Buckley et al. 1996). The hormonally active form of vitamin D (1,25-dihydroxycholecalciferol) is known to increase bone mineralization when given to experimental animals (Cantorna et al. 1998) and people (Ongphiphadhanakul et al. 2000). Thus a further benefit of vitamin D and or 1,25-dihydroxycholecalciferol supplementation may be the maintenance of bone mineral density.

The data suggest that 2-methylene-1 9-nor-vitamin D compounds, and especially 2-MP and 2-MD, are novel and effective treatments for IBD patients. A possible limitation of 2-MD treatment is the hypercalcemia which can result. However, the 2-MP analog is not calcemic and thus may be the treatment of choice because the danger of hypercalcemic is obviated. It is also possible that vitamin D analogs can be used in combination with prior standard treatments for IBD. The standard treatments often work well but have many side effects; like bone loss which some vitamin D analogs such as 2-MD could reverse or block entirely.

Vitamin D analogs in combination with corticosteroids, or sulfasalazine drugs could reduce the effective dose of these drugs, limit side effects and prove to be novel and effective treatments for human IBD.

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 µg to 10 mg per day per 160 pound person of the compounds are appropriate for treatment purposes, such doses being adjusted according to the activity of the particular compound being used, the disease to be treated, its severity and the response of the subject as is well understood in the art. Each compound may be suitably administered alone, or together with graded doses of another active vitamin D compound—e.g. 1α-hydroxyvitamin $D_2$ and/or $D_3$, in combination with 1α,25-dihydroxyvitamin $D_3$—in situations where different degrees of bone mineral mobilization and calcium transport stimulation is found to be advantageous.

Compositions for use in the above-mentioned prevention and/or treatment of IBD comprise an effective amount of one or more vitamin D analog as defined by the above formula I as the active ingredient, and a suitable carrier. An effective amount of such compounds for use in accordance with this invention is from about 0.01 µg to about 100 µg per gm of composition, and may be administered topically, transdermally, orally or parenterally in dosages of from about 0.01 µg/day to about 10 mg/day per 160 pound person.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A method of treating ulcerative colitis comprising administering to a patient with ulcerative colitis an effective amount of 2-methylene-19-nor-20(S)-1α,25-dihydroxy vitamin $D_3$ having the formula:

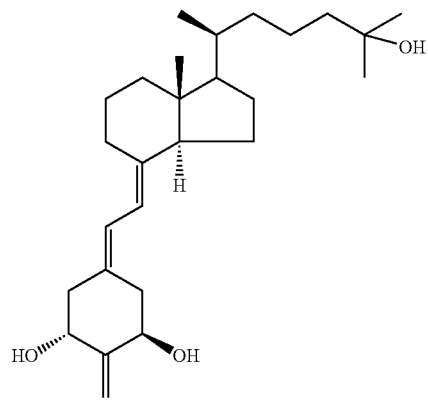

as the only active ingredient.

2. The method of claim 1 wherein the compound is administered orally.

3. The method of claim 1 wherein the compound is administered parenterally.

4. The method of claim 1 wherein the compound is administered transdermally.

5. The method of claim 1 wherein the compound is administered in a dosage of from 0.01 µg to 10mg per day per 160 pound person.

* * * * *